United States Patent [19]

Gregor

[11] 4,033,822

[45] July 5, 1977

[54] ENZYME-COUPLED ULTRAFILTRATION MEMBRANES

[76] Inventor: Harry P. Gregor, 150 Lakeview Ave., Leonia, N.J. 07605

[22] Filed: Nov. 7, 1975

[21] Appl. No.: 629,940

[52] U.S. Cl. .................. 195/68; 195/63; 195/DIG. 11; 195/116; 426/34

[51] Int. Cl.² .......................... C07G 7/02

[58] Field of Search ............ 195/63, 68, DIG. 11, 195/116; 210/490; 426/34

[56] References Cited

UNITED STATES PATENTS

| 3,645,852 | 2/1972 | Axen et al. | 195/63 X |
| 3,705,084 | 12/1972 | Reynolds | 195/63 |
| 3,808,305 | 4/1974 | Gregor | 210/490 X |

OTHER PUBLICATIONS

Thang, et al., Observations on the Activity of Enzymes After Filtration and through) A Nitrocellulose Membrane, Biochem. Biophys. Res. Comm., vol. 31, No. 1, 1968, pp. 1-8.

Inman, et al., The Immobilization of Enyzmes on Xylon Structures and their Use in Automated Analysis, Biochem. J. vol. 129, 1972, pp. 255-262.

*Primary Examiner*—David M. Naff
*Attorney, Agent, or Firm*—Burgess, Dinklage & Sprung

[57] ABSTRACT

Pressure-driven conditions are used to activate and couple enzymes to ultrafiltration membranes such as a homoporous cellulosic membrane having pores of about 15-200 angstroms in diameter. The resultant enzyme-coupled ultrafiltration membranes can be used under pressure-driven conditions for enzymatic conversion of a substrate. The rate of conversion at low substrate concentrations is larger than the rate achieved with the native enzyme.

4 Claims, No Drawings

ENZYME-COUPLED ULTRAFILTRATION MEMBRANES

BACKGROUND OF THE INVENTION

The present invention is directed to the preparation of a class of membranes or filters to which enzymes and other molecules of biological activity are attached by chemical bonds, wherein the process of activation of the membrane pore surfaces (where such is needed) and/or the process of coupling are carried out under the imposition of a pressure gradient across the membrane, and where the utilization of this system can be effected similarly by forcing the substrate to be treated through the membrane pores under pressure. These enzyme-coupled ultrafiltration (hereafter ECUF) membranes are applicable, in principle, to all of those processes wherein enzymes are used, especially when combined with processes of ultrafiltration.

Conventional uses of enzymes employ them in microbial and other cells or as impure or pure soluble enzyme preparations. In recent years enzymes have been entrapped in insoluble gels or coupled chemically to either soluble polyelectrolytes or to insoluble surfaces or within gels of cellulose, glass and other substances. Further, whole cells have been similarly stabilized. It has been found that enzymes stabiled in this manner often show altered characteristics of a favorable nature, in that their effective pH ranges are altered or broadened, their chemical stability is improved as regards chemical (as to urea) and thermal degradation, and thus they can in principle be used for longer periods of time as contrasted to the usages of conventional fermentation processes. All of these advantages are well known and are summerized in various articles and books, especially "Immobilized Enzymes" by O. R. Zaborsky, CRC Press, Cleveland, Ohio 1974.

All of these enzymatic systems and processes may be characterized by the Figure of Merit (FOM) of an enzyme reactor, namely the weight or volume fraction of the reactor which is enzyme, times the ratio of the activity of the same native enzyme in solution at comparable pH and temperature levels. The FOM is proportional to the amount of moles of substrate converted per unit time for given weight or volume of reactor.

The usual process employed heretofore has been to couple enzymes to spherical gel particles of agarose, dextran or of porous glass. These particles are usually quite small, about 20 to 100 microns in diameter to minimize the rate of diffusion as much as is practical. The gel particles of most polymers are quite soft because they are largely water, up to about 95% water in the uncoupled state. Gel particles of glass and other inorganic materials are not soft, but they do not usually contain as large a void fraction.

The usual means of coupling involves reacting the gel bead with an activating chemical or chemicals, removing excess activating chemicals by rinsing the beads for an appropriate period of time, soaking the beads in the enzyme solution whereby the enzyme diffuses into the beads and coupling takes place, following which the unreacted enzyme is flushed from the beads. In use the beads are slurried with the substrate solution or, more frequently, they are placed in a column and the substrate is passed through it. The fineness of the beads produces a low hydraulic permeability for the column and, if one uses a high pressure to increase the rate of throughput, distortion and/or a partial destruction of the beads can result. One can employ filters to separate beads from solution or make the beads dense so a fluidized bed can be operated, but this requires more and expensive equipment and/or a lower loading or % weight or volume % of the system which is enzyme.

While one can coat the outer external surfaces of particles, fibers or films to render the enzyme there readily accessible to the substrate from the solution and thus reduce the time required for diffusion, the loading with enzyme is very low because a thin monomolecular coat of enzyme, even on a rough surface, does not involve a large amount of enzyme.

Further, when enzymes are coupled into gels or entrapped in them by physical means the extent of coupling is not uniform because of the intrinsically random nature of the process so some enzyme molecules are undoubtedly coupled or entrapped less than are others and a leaching or loss of enzyme from the column or bead slurry is usually encountered.

For these reasons, the FOM reported frequently is that corresponding to 3% loading and 3% activity or FOM = $9 \times 10^{-4}$. While some report higher loadings there is usually a loss in activity so a FOM of $10^{-2}$ is considered high. It must be emphasized that the FOM is an operational parameter; it describes the overall activity or rate of conversion of a reactor under conditions of use, not the activity which could be attained if diffusion were not rate-controlling. Indeed, in all but the surface-coated systems, diffusion is almost invariably rate-determining, both in the activation-coupling processes and in processes of use.

It is accordingly an object of the present invention to provide coupled enzyme systems which are useful for a variety of applications, i.e. virtually all of the applications to which stablized enzymes have heretofore been put.

SUMMARY OF THE INVENTION

This and other objects are realized in accordance with the present invention pursuant to which a homoporous matrix membrane of porosity and pore diameter suited for the specific enzyme conditions later to be encountered is activated and then coupled to an enzyme under a pressure such that the maximum operational capacity of the reactor is attained.

The membranes which can be employed in the practice of the invention can be of any known type, although cellulosic membranes have proven especially effective.

The matrix membrane or filter must have properties compatible to its use. It should be of sufficient porosity so the substance or substances of biological activity can be introduced therein from an ambient solution or suspension phase. It should have sufficient mechanical strength (or be capable of being supported mechanically) so as to withstand the pressure gradients which are applied across it during processing and under conditions of use. In addition, it must have a multitude of small pores so at to have a large effective surface which, ultimately, will be lined with the enzymes. The pores advantageously range in size from about 3 to 5 times the enzyme diameter. Smaller pores either cannot receive the enzymes or, after a single enzyme enters, it blocks and/or damages other enzymes which might enter. Larger pores can accept enzymes but the relative amount of pore surface per unit mass of membrane is far smaller than with pores of the preferred size range. The exact pore size will thus depend upon the size of the enzyme to be coupled. Most enzymes range in molecular weight from about 10,000 to 1,000,000 and in diameter from about 5 to 75 Angstroms so membranes with pores of about 15 to 200 Angstroms are preferred. Pore diameters as employed herein are measured according to the Ferry-Faxen equations as described in H. Kawabe et al, J. Colloid and Interface Science Vol. 21 (1966) 79, viz. molecules of different size are allowed to diffuse across the membrane and from the rate of diffusion the effective average pore diameter is calculated.

In order to optimize the system with respect to the membrane or filter matrix, it is preferred that it be as homoporous as is practical so as to obtain as high an available pore surface area per unit volume. To this the preparative procedures generally described by W. J. Elford (Proc. Roy. Soc. Ser.B., Vol. 106 (1930) 216 are quite suitable, i.e. a film is cast from a solvent or solvent mixture, some solvent is allowed to evaporate to set the polymer gel, then it is coagulated to produce a membrane of desired porosity.

The pore surfaces of the matrix membrane or film can already carry active or reactive groups for attachment to enzymes or they can be treated in known manner to provide such groups. Such activation processes are advantageously carried out under pressure-driven conditions, especially where unstable substituents or by-products are involved, because the residence time of reactants in the membrane or filter can be controlled at will. The use of rapid displacement processes is a particular feature of this invention. For example, superior systems result when, after activating a regenerated cellulose membrane with cyanogen bromide at pH 11, excess reactant is rapidly washed away with water and the enzyme solution is forced into the pores of the film substantially immediately thereafter. When these teachings are employed, systems of superior activity result, for reasons which are not wholly clear. While water can decompose the cyanogen bromide activator and while the enzymes may be unstable at pH 11, the repidity of processing, particularly due to the use of pressure, does not permit decomposition of the cyanogen bromide and/or enzyme to occur to any significant extent before the enzyme is attached to the membrane and the conditions no longer favor decomposition.

Any superatmospheric pressure can be employed to accelerate the passage of activating liquid and/or of enzyme through the membrane although a pressure of at least about 10 psig, especially about 30 to 120 psig, gives particularly good results. The pressure or potential, instead of being of a pneumatic or hydraulic type, can be of an electrical nature, i.e. as in the well-known phenomenon of electroosmosis and/or electrophoresis wherein an electric potential is imposed across a membrane or filter and combinations of the activation-coupling and use operations effected in that manner. Thus, for example, with chymotrypsin coupled following activation with cyanogen bromide a current which produces a flow of solution through the membrane comparable to that due to a pressure gradient of 70 psi produces a system whose enzymatic activity is nearly the same as one prepared under 70 psi.

The membranes which are activated and coupled to enzymes in accordance with the present invention can be in any physical form, e.g. sheets, tubelets, fine hollow fibers and the like. When prepared as described, cellulose having chymotrypsin coupled thereto, for example, has given a FOM as high as 0.15, corresponding to a weight loading of 20% and an activity of 75%. Comparable results were obtained with beta-galactosidase from E. coli, and the teachings of this invention can be applied to a host of enzymes and other biological substances. These FOM are often 100 times those for the enzymatic reactors of the prior art and the rates of reaction with substrate are often higher than the rate in solution. This means that the "turn-over" rate with such enzymes is more rapid and means that substrate solutions too dilute to be treated in an effective manner by conventional reactors can be effectively treated by the systems of the present invention.

As noted, one advantage to the systems prepared by the teachings of this invention is that they possess a rate of enzymatic conversion at low substrate concentrations which is larger, ofter several times larger, than the rate achieved under comparable conditions with the native enzyme. The reasons for this are not at all clear, but the effects are real. The existence of these effects may be shown by measuring rate of conversions at a constant pH, temperature, and also at constant pressure in the region where changes in pressure have little effect on rates, but at different substrate concentrations. In the case of pressure-driven CNBr activation and coupling chymotrypsin (CT) at 70 psig, using the well-known BTEE (benzoyl tyrosine ethylester) hydrolysis test of Hummel (Can J. Biochem. Physio. Vol. 37 (1959) 1393) there is obtained a rate of 27 $\mu$ moles/-min.mg of 34 ml of enzyme when the substrate concentration is high at $5.2 \times 10^{-4}$ M, at a level where substrate concentration is no longer rate-controlling. This rate is 75% of the maximum rate ($V_{max}$) of the same amount of native enzyme at the same concentration. However, when the substrate concentrate is low at $0.2 \times 10^{-4}$M when the rate is increasing linearly with substrate concentration, there is obtained a rate of conversion of 12 $\mu$ moles /min.mg for the systems perpared under the teachings of this invention as compared to a rate of 0.15 $\mu$ moles/min.mg for the native enzyme. This 80-fold increase in the rate represents a substantial advantage to these novel systems. It means, for example, that this enzyme system can be used to treat very dilute solutions and obtain a FOM greater than that of the native enzyme.

It is important that the teachings of this invention be employed in a manner appropriate to the substance of biological activity which is involved in its use. For example, one should not employ pressures which are too high during the processes of coupling and/or use because deleterious effects can result. For example, fragile enzymes that as the $\beta$-galactosidases are denatured irreversibly when coupling is carried out at too high a pressure. It is postulated that shear degradation occurs under these circumstances. Similarly, if certain substrates are used with membranes of too fine a pore structure, the coupled enzymes can be damaged or destroyed. For example, by forcing a protein solution such as that of casein through a cellulose membrane having pores about 80 Angstroms in diameter and coupled with CT, the enzyme activity can be reduced irreversibly. In short, one must apply the teachings of this invention with the knowledge of one skilled in the arts of biochemistry.

The use of the membranes or filters of $\beta$-galactosidase invention may be considerably facilitated by the employment of a prior ultrafiltration of the substrate solution through membranes which remove substances of a size or nature which act to clog, foul or destroy the enzyme-couples systems of this invention. The non-fouling ultrafiltration membranes of fixed-charge character as described in U.S. Pat. No. 3,808,305 are particularly useful in this respect. For example, if one wishes to cleave the lactose in a whey or skim milk solution, ultrafiltration acts to remove those colloidal impurities present which can damage the fragile B-galactosidase enzyme employed for this purpose. Accordingly, the utility of the systems of this present invention is expanded by a prior ultrafiltration through membranes of appropriate properties.

The following examples are provided to illustrate the invention more fully. It will be understood that, because the examples are illustrative, they are not to be construed as limiting the invention, except as defined by the appended claims. All parts are parts by weight, except where otherwise expressly stated. The notation employed in this application and certain of the procedures employed are the same as those of U.S. Pat. No. 3,808,305.

EXAMPLE I

A matrix membrane was cast from a 15% solution of Eastman cellulose acetate (39.4% acetyl, viscosity 45) in a DMF (dimethylformamide): acetone mixture (1:3.25 by volume) at room temperature onto a glass plate with a doctor blade of gate opening of 300 microns. The film was allowed to evaporate in the air for 3 minutes, then kept in a closed container for 1 hour to eliminate any appreciable "skin" formation and then coagulated by exposure to water vapor in the closed container for 15 minutes, followed by immersion in water at room temperature for 2 minutes, then in ice water for 1 hour. These were regenerated to cellulose by conventional hydrolysis in a buffer at pH 9.9 for 24 hours at 65° C. The final films had a wet thickness of 30 microns, a water content of 80-87% and a hydraulic permeability (HP) of 0.001-0.002 cm/sec atm. These films were activated with a solution of 40 mg CNBr in 100 ml of water at pH 11 (with NaOH) forced through at 70 psig, and excess CNBr was removed by a 1 minute rinse with water, repeated with 0.1 M $NaHCO_3$, all at 70 psig, and immediately treated with a solution of 40 mg of chymotrypsin (Sigma Chem. Co., 3× crystallized from 4× crystallized CT, dialyzed salt-free and lyophilized) in 100 ml 0.1 M $NaHCO_3$ at 4° C., also at 70 psig, following which the membrane was incubated in the effluent for 24 hours at 4° C., then washed with distilled water. The final membrane contained 241 mg enzyme/g of dried membrane, i.e. 24% loading. It retained its original HP, was now 33 microns thick with a water content of 73-80%. Membranes were stored at 4° C. in distilled water. The activity of this membrane was determined by the method of Hummel using 0.00107 M BTEE, wherein the substrate was forced through the membrane mouted in a Millipore cell at 25° C., with a pressure of 100 psi applied by nitrogen gas and the assay performed in the downstream effluent. It was found that under these conditions the measured activity (as determined by the amount of substrate converted per unit time) was 75% of that of the same amount of native enzyme measured with the same substrate under conventional conditions. Accordingly, the FOM for this system was 0.24 × 0.75 or 0.18 . Other data and properties of systems prepared from the same cellulosic matrix membranes by different combinations of preparation pressures and substrate pressures are presented in Table I hereinbelow.

EXAMPLE II

Using the same matrix cellophane membrane of Example I mounted in a 4 chamber cell containing two end electrode compartments separated from the two central compartments by commercially available cation-exchange membranes (Asahi Chemical Industries membranes DK-1), with the matrix membrane separating the two central compartments, and where a CT solution in 0.001 M KCl at pH 8.7 at an enzyme concentration of 2 mg/ml was in one of the two central compartments, an electric current was applied such that the voltage gradient across the membrane corresponded to 20 V/cm and the enzyme solution was thus forced through the membrane at a rate approximately equal to that of a pressure of 70 psig. The enzyme membrane was then removed from the cell, incubated at 4° C. for 24 hours as in Example I, then stored for use. This system showed a loading of 20% enzyme and an activity of 70% of that of the native enzyme when tested by BTEE as in Example I in the pressure cell at 100 psig substrate pressure.

EXAMPLE III

A membrane was cast from cellulose acetate as in Example I but kept in the closed container for 0.5 hour. Then water was introduced into the chamber below the supported film but not in contact therewith the film was so kept for 30 minutes. It was then quickly sprayed with a fine water spray until wet and placed in ice-water for one hour to complete the coagulation. After hydrolysis it was 29 microns in thickness, had a water content of 77% and a HP of 0.01-0.08 cm/sec atm. The film was activated with CNBr as in Example I but at 15 spig using 100 ml of the CNBr solution, then washed quickly with water and then with a cold oxygen-free solution of 20 mg β-galactosidase (Worthington, E. coli K12, purified) in 50 ml of 0.1 M phosphate buffer at 15 psig also oxygen-free, all performed rapidly. The membrane was then immersed in the effluent from the coupling reaction overnight at 4° C. It was then re-mounted in the cell and then an oxygen-free 0.8% solution of lactose, buffered to pH 7.5, was forced through the membrane at 30 psig and the effluent analyzed for glucose by the standard Glucostat procedure. The activity of the coupled enzyme was 30 times that of the native enzyme and its loading of 50% gave a FOM of 21. It is believed the activity in excess of 100% is due to a selective coupling of pure enzyme from the impure mixture of native enzyme.

EXAMPLE IV

The membrane of Example III was used to treat lactose from skim milk. Fresh skim milk was treated with dilute NaOH and zinc chloride and centrifuged to remove all milk solids and then passed through the membrane at 37° C. at psig. The activity observed by Glucostat analysis was 80% of the activity towards pure lactose.

Table I

| EFFECT OF ACTIVATION-COUPLING PRESSURE OF CHYMOTRYPSIN COUPLED TO CELLULOSE | | | | |
|---|---|---|---|---|
| Activation Pressure (psig) | Coupling Pressure (psig) | Protein Bound (mg/g) | Substrate Pressure (psig) | Activity (%) |
| 0 | 0 | 215 | 0 | 1.0 |

Table I-continued

EFFECT OF ACTIVATION-COUPLING PRESSURE OF CHYMOTRYPSIN COUPLED TO CELLULOSE

| Activation Pressure (psig) | Coupling Pressure (psig) | Protein Bound (mg/g) | Substrate Pressure (psig) | Activity (%) |
|---|---|---|---|---|
| | | | 10 | 2.0 |
| | | | 50 | 9.0 |
| | | | 80 | 19.0 |
| | | | 100 | 28.0 |
| | | | 120 | 40.0 |
| 10 | 10 | 205 | 0 | 2.0 |
| | | | 10 | 4.0 |
| | | | 50 | 15.5 |
| | | | 80 | 26.5 |
| | | | 100 | 38.0 |
| | | | 120 | 42.5 |
| 30 | 30 | 243 | 0 | 3.0 |
| | | | 10 | 7.0 |
| | | | 50 | 22.5 |
| | | | 80 | 32.0 |
| | | | 100 | 45.5 |
| | | | 120 | 50.5 |
| 50 | 50 | 224 | 0 | 4.0 |
| | | | 10 | 9.0 |
| | | | 50 | 30.0 |
| | | | 80 | 47.5 |
| | | | 100 | 58.5 |
| | | | 120 | 62.5 |
| 70 | 70 | 241 | 0 | 7.0 |
| | | | 10 | 14.0 |
| | | | 50 | 53.0 |
| | | | 80 | 70.0 |
| | | | 100 | 74.5 |
| | | | 120 | 74.5 |
| 90 | 90 | 213 | 0 | 6.0 |
| | | | 10 | 13.5 |
| | | | 50 | 53.0 |
| | | | 80 | 69.0 |
| | | | 100 | 72.0 |
| | | | 120 | 74.5 |
| 110 | 110 | 248 | 0 | 5.0 |
| | | | 10 | 10.0 |
| | | | 50 | 47.5 |
| | | | 80 | 63.0 |
| | | | 100 | 70.0 |
| | | | 120 | 70.0 |
| 0 | 50 | 220 | 120 | 23.0 |
| 50 | 0 | 160 | 120 | 50.0 |

It will be appreciated that the instant specification and examples are set forth by way of illustration and not limitation, and that various modifications and changes may be made without departing from the spirit and scope of the present invention.

What is claimed is:

1. A process for producing an enzyme-coupled ultrafiltration membrane comprising forcing a solution of cyanogen bromide under a pressure equivalent to at least about 30 psig through a homoporous cellulosic ultrafiltration membrane having pores of about 15 to 200 Angstroms in diameter thereby to form activated sites within such membrane, washing away excess cyanogen bromide and forcing a solution of chymotrypsin or beta-galactosidase through said membrane under a pressure equivalent to at least about 10 psig, the activated sites being reactive with said enzyme thereby to couple said enzyme to said membrane.

2. The process of claim 1 wherein said membrane has pores averaging in size from about 3 to 5 times the diameter of said enzyme.

3. The process of claim 2, wherein the activated membrane is produced by forcing cyanogen bromide through said membrane under a pressure equivalent to about 70 to 120 psig, and the enzyme is forced through said membrane under a pressure equivalent to about 30 to 120 psig.

4. The process according to claim 3, wherein the enzyme in said solution is impure, the activated membrane selectively extracting the enzyme from its solution so that the enzyme is concentrated simultaneously with its coupling.

* * * * *